United States Patent
Adair et al.

(10) Patent No.: US 7,892,487 B2
(45) Date of Patent: Feb. 22, 2011

(54) USEFUL LIFE INDICATORS

(75) Inventors: Joel E. Adair, Racine, WI (US); Kwamena Gyakye deGraft-Johnson, Racine, WI (US); Anne T. Maghasi, Racine, WI (US); Brian T. Davis, Burlington, WI (US); Donald J. Schumacher, Racine, WI (US); Padma Prabodh Varanasi, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1105 days.

(21) Appl. No.: 11/609,923

(22) Filed: Dec. 13, 2006

(65) Prior Publication Data

US 2008/0141928 A1 Jun. 19, 2008

(51) Int. Cl.
*A61L 9/03* (2006.01)
*A61L 9/12* (2006.01)

(52) U.S. Cl. .............................. 422/55; 239/34; 239/35; 239/53

(58) Field of Classification Search ................. 239/35, 239/34, 53; 422/55
See application file for complete search history.

(56) References Cited

U.S. PATENT DOCUMENTS

| | | | |
|---|---|---|---|
| 2,923,157 A | 2/1960 | Peifer | |
| 3,417,730 A | 12/1968 | Colley et al. | |
| 4,824,827 A | 4/1989 | Kelly et al. | |
| 4,921,636 A | 5/1990 | Traas | |
| 5,293,648 A | 3/1994 | Finley | |
| 5,385,044 A | 1/1995 | Thomas et al. | |
| 5,388,331 A | 2/1995 | Siamak | |
| 5,538,161 A | 7/1996 | Koehler et al. | |
| 6,031,967 A | 2/2000 | Flashinski et al. | |
| 6,790,670 B2 | 9/2004 | Munagavalasa et al. | |
| 7,007,861 B2 | 3/2006 | Ketcha et al. | |
| 7,165,466 B2 * | 1/2007 | Jensen et al. | 73/866 |
| 2003/0168521 A1 * | 9/2003 | Skalitzky et al. | 239/57 |
| 2004/0151747 A1 | 8/2004 | Davis et al. | |
| 2004/0247301 A1 * | 12/2004 | Yip et al. | 392/395 |
| 2006/0193611 A1 * | 8/2006 | Ruiz Ballesteros et al. | 392/394 |
| 2008/0056691 A1 * | 3/2008 | Wingo et al. | 392/395 |

FOREIGN PATENT DOCUMENTS

| | | |
|---|---|---|
| CH | 217531 | 10/1941 |
| EP | 0227167 | 7/1987 |
| GB | 2397022 A | 6/2004 |
| WO | WO2007/089928 A1 | 8/2007 |

OTHER PUBLICATIONS

U.S. Appl. No. 11/346,697, filed Feb. 3, 2006, Joel E. Adair.
PCT/US2007/025521 International Search Report and Written Opinion dated May 16, 2008.

\* cited by examiner

*Primary Examiner*—In Suk Bullock
*Assistant Examiner*—Paul S Hyun

(57) ABSTRACT

A useful life indicator is provided to display an indication of the remaining useful life of an associated product such as an impregnated substrate of an air treatment chemical dispenser. The cue is preferably a well having a volatile indicator material positioned therein. The well's cavity is configured to achieve clumping of the remaining indicator material as some volatizes due to capillary attraction. This presents a shrinking display that can be coordinated with the level of use of the air treatment chemical dispenser. The cue may also be used in connection with monitoring other products such as perishable products.

12 Claims, 7 Drawing Sheets

USEFUL LIFE INDICATORS

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to indicator devices that display information about the extent of remaining useful life of associated products. These indicator devices are particularly well suited for use with air treatment chemical dispensers.

Many products have a useable life dependent upon the time the product is exposed to a surrounding environment and/or operated. For example, a variety of products are designed to dispense air treatment chemicals from an impregnated substrate. Sometimes the evaporation is assisted by heating the substrate. Other times it is assisted by having a fan or other device blow air across the substrate. In still other cases the air treatment chemical can volatize even without the assistance of heating or blown air (e.g. passive evaporation).

Unfortunately, such evaporation typically will not alter the visible appearance of the substrate. Moreover, even if it did, these substrates are sometimes housed internally within such devices where they cannot be easily visually monitored. This makes it difficult to know when the substrate is near the end of its useful life.

In a variety of other contexts it is similarly valuable to be able to monitor the status of products where the product itself does not accurately visually disclose that information. For example, food products will often degrade over time. While many food products will exhibit this degradation in a visually perceptible manner, for some the freshness will not be evident from visible changes in the product itself.

A variety of methods and devices have been developed to alert consumers as to the status of products. For example, packaging for some products includes a date stamp indicating the estimated end of the useable product life. However, consumers may not read or remember that information. Further, given the wide range of conditions to which such products may be exposed, suggested useful life information may not be accurate in many cases. This can lead to use of the product after its effective useful life (with resulting consumer dissatisfaction). Alternatively, it can lead to premature disposal of a still useful product (and thus unnecessary cost and waste).

A wide variety of gauges and other devices have been developed to provided use-up/useful life information. See generally U.S. Pat. Nos. 2,923,157, 3,417,730, 4,921,636, 5,923,648, 5,385,044, 5,388,331, and 5,538,161. See also U.S. Pat. No. 4,824,917 (evaporation of a solvent leads to a color change); and U.S. Pat. No. 6,790,670 (evaporation of a dye leads to a color change). See also S.C. Johnson & Son's U.S. Ser. No. 11/346,697 filed on Feb. 3, 2006 (volatile indicator material held separately from volatile air treatment chemical, but with rates of volatilization coordinated).

While these devices do provide improved monitoring of the product status, the inexpensive ones are typically designed to identify the final use-up point, rather than displaying information about the degree of use-up. In this regard, it is one thing to have an indicator that displays a warning near or at the use-up point. It is another to also be able to have more specific indications about the extent of partial use, particularly where this can be achieved at low cost.

Thus, a need exists for improved automatic useful life indicators, particularly where such indicators are capable of providing detailed information about the state of partial use-up without requiring complex or expensive structures to achieve this advantage.

BRIEF SUMMARY OF THE INVENTION

The present invention comprises useful life indicators that use capillary attraction to create informative indicator displays. One form of the invention provides a useful life indicator having a well with an internal cavity and a volatile indicator material positioned within the cavity. Preferably, the volatile indicator material is a flowable material such as a liquid or flowable gel.

The well is configured to cause a remaining portion of the volatile indicator material to clump (e.g. adhere) together once another portion of the original volatile indicator material in the cavity has volatized from the well, such that a portion of the cavity that prior to the volatization observably contained volatile indicator material now appears essentially volatile indicator material free. In preferred forms the well has a semi-permeable membrane, the volatile indicator material being capable of passing through the semi-permeable membrane preferably only in the vapor phase, and the semi-permeable membrane has an outer peel-off cover removably positioned over the membrane.

A variety of configurations for the well are disclosed resulting in varied display forms. For example, the indicator could create a display in the form of a rectangle, or in the form of a gauge, or one thermometer shaped, or one that appears spiral or clock-shaped, or one that appears spot-shaped.

Regardless, it is desired that capillary attraction causes clumping/adhesion of remaining volatile indicator material after a portion of the volatile indicator material volatizes out of the well. This creates a shrinking display effect. It can occur with narrow and elongated well cavities. It can also occur where the well has a shallow portion and a deeper portion, where during use volatile indicator material volatizes in a manner that exposes a floor of the deeper portion before exposing a floor of the shallower portion.

In another aspect of the invention there is provided an air treatment control device. It has an impregnated substrate, a separate well, or other holding means for holding and/or dispensing an air treatment chemical and a use-up cue. The cue preferably has a well with an internal cavity, and a flowable volatile indicator material positioned within the cavity. The well is configured to cause a remaining portion of the volatile indicator material to clump/adhere together once another portion of the volatile indicator material in the cavity has volatized from the well, such that a portion of the cavity that prior to the volatization observably contained volatile indicator material now appears essentially volatile indicator material free.

In preferred forms of this aspect the use-up cue is coordinated with the holding means for holding an air treatment chemical such that changes in the use-up cue are indicative of the extent of use-up of the air treatment chemical. A fan and/or a heater can be provided to motivate volatization from the holding means, the well, and/or both.

Such useful life indicators are inexpensive to produce, thereby rendering them practical for a variety of applications. Further, they not only provide information about the end of a useful life of a product, they also provide relatively detailed information about the degree to which the use-up is approaching throughout the useful life of the product.

In another aspect of the invention, a method is provided for indicating a remaining amount or remaining useful life of an air treatment chemical being dispensed by an air treatment control device. The method comprises a first step of providing a use-up cue having a well with an internal cavity and a flowable volatile indicator material positioned within the cavity, with a semi-permeable membrane covering the cavity, the membrane being impermeable to the volatile indicator material when in flowable form but permeable to the volatile indicator material in vapor form so that the volatile indicator material is volatilized from the well at a controlled rate.

The well of the use-up cue so provided is configured so as to cause a remaining portion of the volatile indicator material to clump together once another portion of the volatile indicator material in the cavity has volatized from the well, such that a portion of the cavity that, prior to said volatization, observably contained volatile indicator material appears essentially volatile indicator material free. The use-up cue so provided further includes a removable cover preventing loss of the volatile indicator material through the membrane until the cover is removed.

A preferred aspect of the method comprises removing the cover essentially simultaneously with when dispensing of the air treatment chemical is begun, the volatile indicator material and the membrane being so selected that the observable remaining portion of the volatile indicator material visually correlates with the remaining amount of air treatment chemical to be dispensed.

The foregoing and other advantages of the present invention will be apparent from the following description. In the description that follows reference is made to the accompanying drawings which form a part thereof, and in which there is shown by way of illustration, and not limitation, expected preferred embodiments of the invention. Such embodiments do not necessarily represent the full scope of the invention, and reference should therefore be made to the claims herein for interpreting the scope of the invention.

DETAILED DESCRIPTION OF THE PREFERRED EMBODIMENTS

The present invention relates to useful life indicators dimensioned to utilize cohesion/adhesion (a/k/a "capillary attraction"), to manipulate the pattern left by a flowable volatile indicator material as a portion of it volatizes. It has been discovered that through appropriate sizing and shaping of the cavity holding the material capillary attraction can cause the remaining use-up cue material to be drawn together, leaving a visible indication of the degree of use-up.

Capillary attraction can be used to draw the remaining indicator material into a narrow section of the holding cavity. Alternatively, or in addition, it may be used to draw the remaining portion into the most shallow portion of the cavity, even against the force of gravity.

Figure 1A:
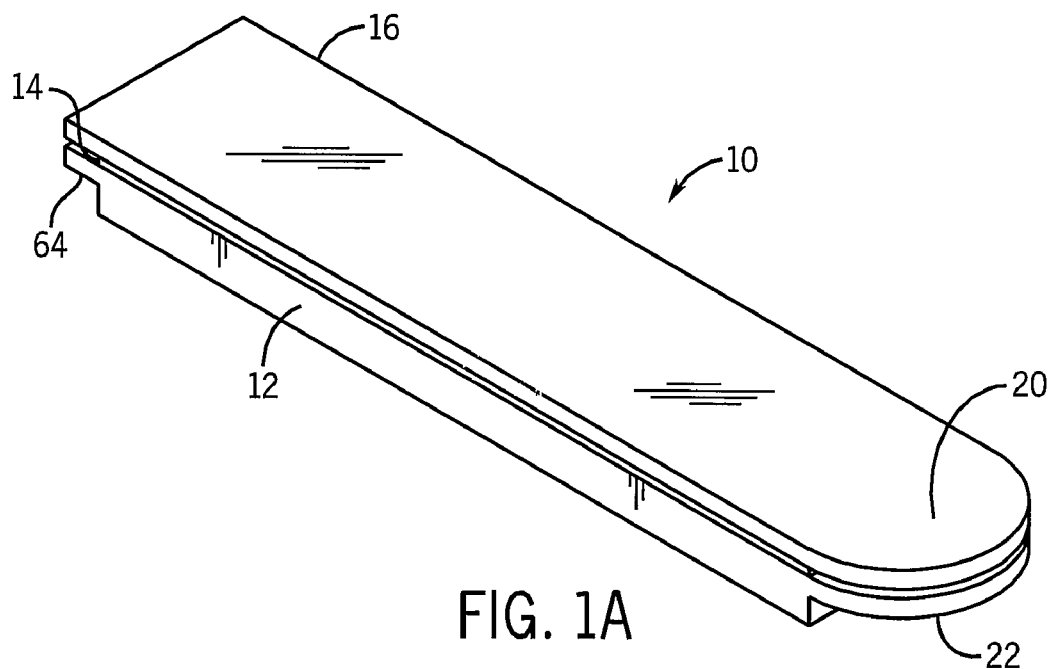
FIG. 1A is a perspective view of a first embodiment of the present invention.
Figure 1B:
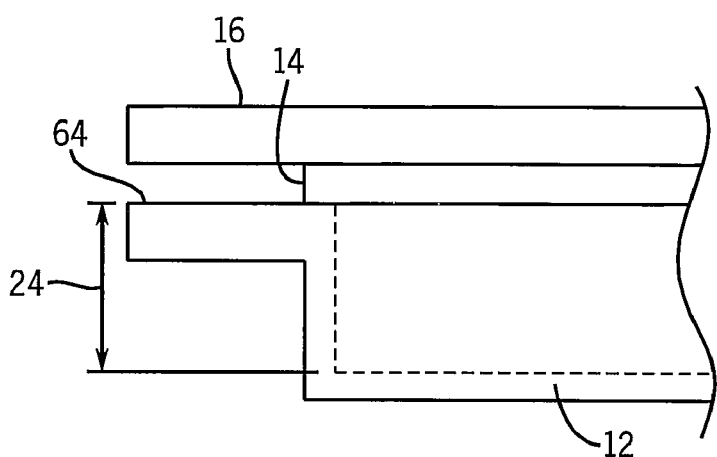
FIG. 1B is a partial section view of the use-up cue of FIG. 1A.
Figure 2A:
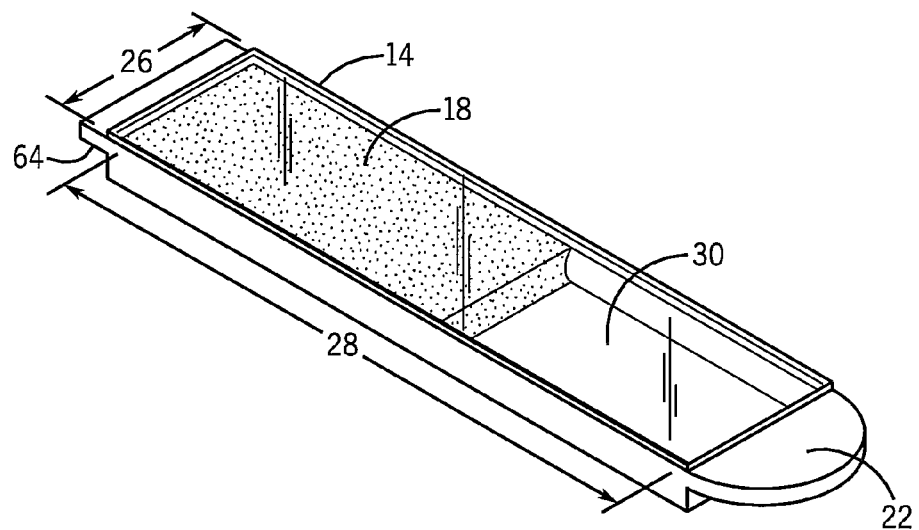
FIG. 2A is a perspective view of the use-up cue of FIG. 1A, but with a peel-off cover removed.
Figure 2B:
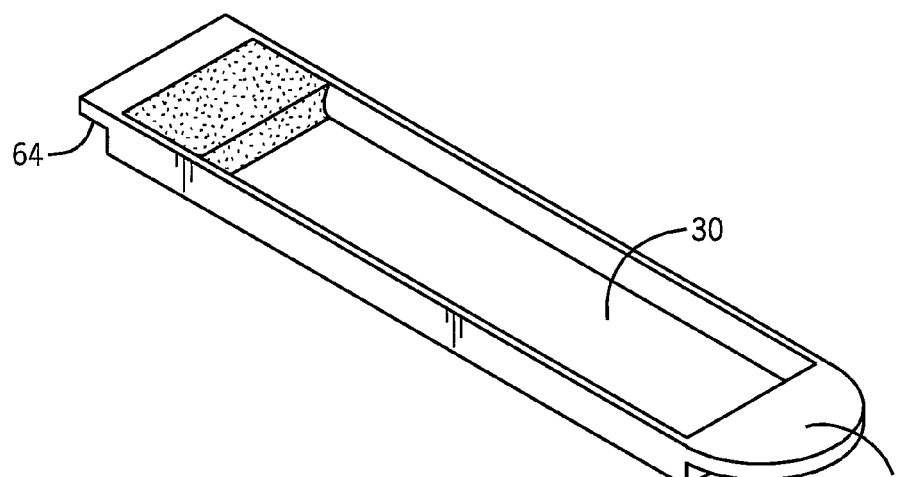
FIG. 2B is a perspective view similar to FIG. 2A, but after additional use.
Figure 3A:
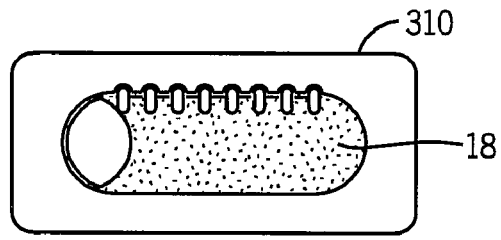
FIG. 3A is a top view of a third embodiment prior to use.
Figure 3B:
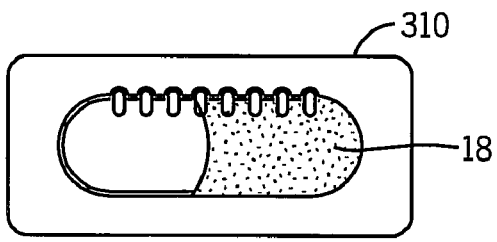
FIG. 3B is a view similar to FIG. 3A, but showing the device indicating partial use.
Figure 3C:
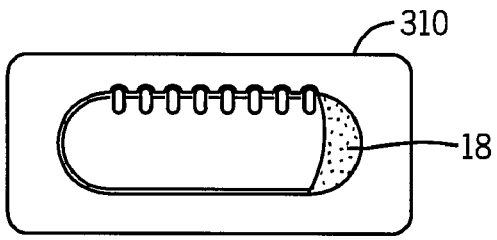
FIG. 3C is a view similar to FIG. 3A, but showing the device indicating almost a used-up condition.
Figure 3D:
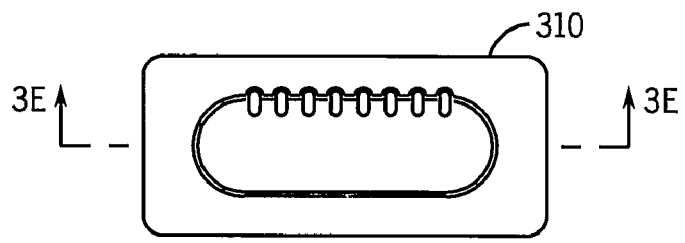
FIG. 3D is a view similar to FIG. 3A, but showing the device indicating a complete use-up condition.
Figure 3E:
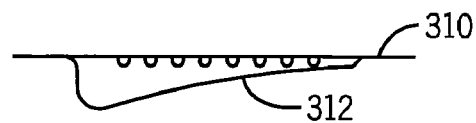
FIG. 3E is a section view taken along line 3E-3E of FIG. 3D.
Figure 5A:
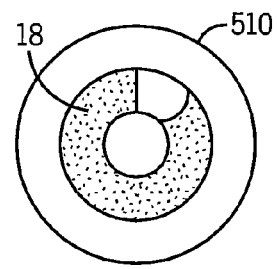
FIG. 5A is a top view of another embodiment prior to use.
Figure 5B:
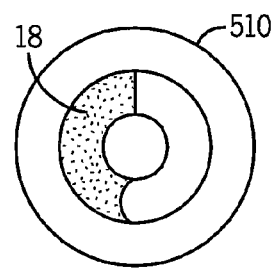
FIG. 5B is a view similar to FIG. 5A, but showing the device indicating partial use.
Figure 5C:
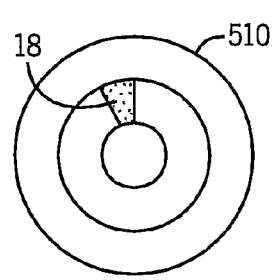
FIG. 5C is a view similar to FIG. 5A, but showing the device indicating almost a used-up condition.
Figure 5D:
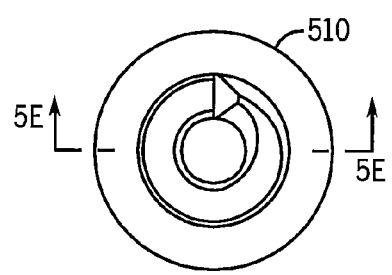
FIG. 5D is a view similar to FIG. 5A, but showing the device indicating a complete use-up condition.

FIGS. 1A and 1B show one type of elongated use-up cue 10 which has a well 12, a semi-permeable membrane 14, and a peel-off cover 16. The peel-off cover 16 is removed when the product is first placed in use so as to expose the semi-permeable membrane 14 covering the indicator material 18 (the latter being shown in FIGS. 2A and 2B) to the environment (the indicator material 18 may diffuse past the semi-permeable membrane 14 once the peel-off cover 16 is removed).

The peel-off cover 16 has a tab section 20 extending over another tab 22 of the use-up cue 10, to facilitate gripping of the peel-off cover 16. The peel-off cover 16 is preferably impermeable to the vapor of the volatile, for example, a thin metal film or impermeable plastic may be used. The peel-off cover 16 may optimally be configured to be reapplied to the use-up cue 10. While the product is operating, the cover can be off, and the cover can optionally be replaced between uses of the device.

U.S. Pat. No. 6,031,967 generally describes units designed to permit volatiles to be dispensed from wells having peel-off covers (albeit in this patent the well contains the air treatment chemical). The materials used therein, apart from the air treatment chemical, could be applied here.

In this regard the well can be made from a plastic such as polyethylene terephthalate, and be provided with an integral surrounding upper flange. One possible peel-off cover 16 would have an outer polyester layer, under which is positioned a low density polyethylene layer, under which is positioned an aluminum foil layer, under which is positioned polypropylene, under which is positioned low density polyethylene material.

Although a cover 16 that can be peeled off is the preferred embodiment, rigid or other cover configurations are also possible so long as they can be removed or opened without damage to the semi-permeable membrane 14. Such alternative covers could simply be removed or could slide to one side, be hinged, or otherwise be configured so as to be openable and even to be reclosable.

A variety of semi-permeable membranes 14 are possible, such as those of natural, semisynthetic, or synthetic origin. Examples include polyethylene, polypropylene, ethylene/vinyl acetate copolymer, polyvinyl chloride, and polyurethane films.

The indicator material 18 may be liquid or a flowable gel. It may be passively volatile (i.e., it volatizes by simply being exposed to the environment), or instead be motivated largely by a means such as heater or a fan, or some combination thereof. Most preferably the volatile is a colored liquid to facilitate viewing. In experiments, Norpar 12 (a hydrocarbon) from ExxonMobil Chemical Company was successfully tested as one possible effective indicator material 18.

Other preferred indicator materials 18 are those containing guaiazulene dye materials described in U.S. Pat. No. 6,790, 670. This patent describes a variety of ways of precisely controlling the speed of volatilization (e.g., using retarders and solvents, among other means). This will facilitate coordinating the rate of release with the rate of release of the air treatment chemical.

While the well 12 is shown as shallow and narrow front-to-back, and thus able to develop capillary attraction, a variety of other well shapes are possible. Generally, the presence of shallow areas less than 3 mm deep and/or narrow areas of less than 3 mm wide will create a sufficient tendency for capillary attraction of the remaining liquid as fluid levels drop due to volatilization. In the FIG. 1B embodiment, well 12 had a length of 17 mm, a uniform width of 2.5 mm, and a uniform depth of 2 mm.

FIGS. 3A-7E depict additional embodiments and are discussed below. In each case, the well is configured with narrow and/or shallow sections sufficient to cause the remaining liquid to clump together via capillary attraction in the narrow and/or shallow regions.

As the indicator material 18 volatizes through the semi-permeable membrane 14, the remaining indicator material 18 will pool together and more importantly create an ever increasing region of essentially no volatile which is easily visually identified. In the first embodiment, the clumping could occur to the left, or to the right, or even somewhere in between, given the uniformity of the dimensions. In any event, the unified pool/clump will appear to the consumer as a shortening line. (Compare FIGS. 2A and 2B).

The device 310 of FIGS. 3A-3E appears almost gauge-like with the remaining liquid clumping towards the shallow floor 312. The indicator material 18 appears to the consumer to recede from the left, deeper end of the well towards the right, shallower end. Therefore, as volatilization occurs, the user can view the use-up cue device 310 and have a better understanding of the remaining associated product life when the cue is coordinated with a product like that of FIG. 8. For example, FIG. 3B could indicate that the product still has approximately one-half of its life remaining.

Figure 4A:
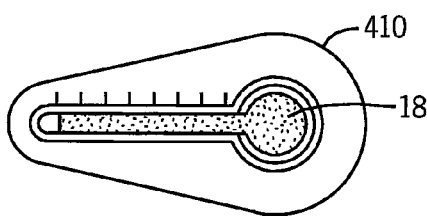
FIG. 4A is a top view of a fourth embodiment prior to use.
Figure 4B:
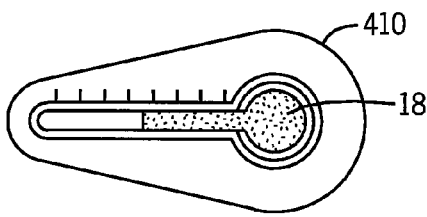
FIG. 4B is a view similar to FIG. 4A, but showing the device indicating partial use.
Figure 4C:
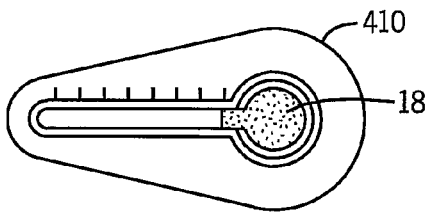
FIG. 4C is a view similar to FIG. 4A, but showing the device indicating almost a used-up condition.
Figure 4D:
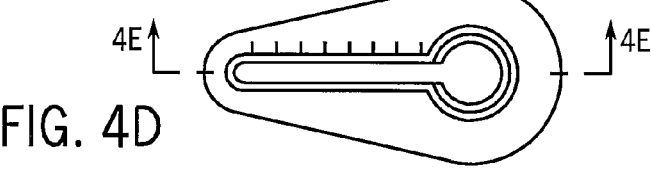
FIG. 4D is a view similar to FIG. 4A, but showing the device indicating a complete use-up condition.
Figure 4E:
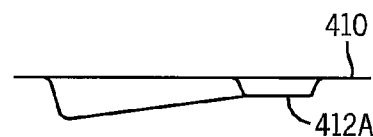
FIG. 4E is a section view taken along line 4E-4E of FIG. 4D.
Figure 4F:
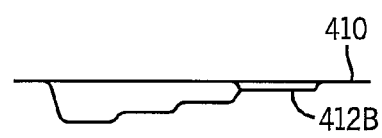
FIG. 4F is a view similar to FIG. 4E showing a modified bottom wall structure in an alternative embodiment.
Figure 4G:
FIG. 4G is another view similar to FIG. 4F showing a further modified bottom wall structure in yet another alternative embodiment.
Figure 5E:
FIG. 5E is a section view taken along line 5E-5E of FIG. 5D.
Figure 6A:
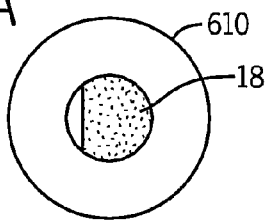
FIG. 6A is a top view of yet another embodiment prior to use.
Figure 6B:
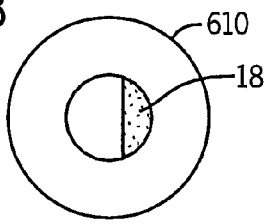
FIG. 6B is a view similar to FIG. 6A, but showing the device indicating partial use.
Figure 6C:
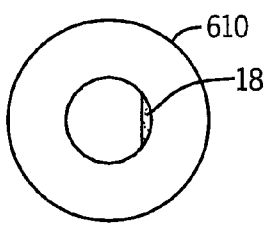
FIG. 6C is a view similar to FIG. 6A, but showing the device indicating almost a used-up condition.
Figure 6D:
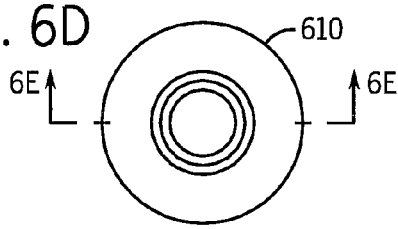
FIG. 6D is a view similar to FIG. 6A, but showing the device indicating a complete use-up condition.
Figure 6E:
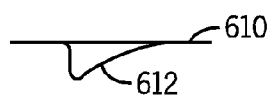
FIG. 6E is a section view taken along line 6E-6E of FIG. 6D.
Figure 7A:
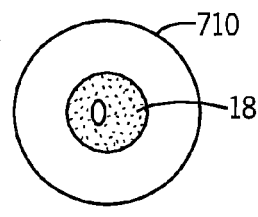
FIG. 7A is a top view of still another embodiment prior to use.
Figure 7B:
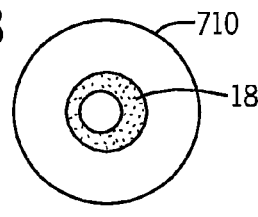
FIG. 7B is a view similar to FIG. 7A, but showing the device indicating partial use.
Figure 7C:
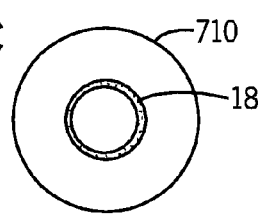
FIG. 7C is a view similar to FIG. 7A, but showing the device indicating almost a used-up condition.
Figure 7D:
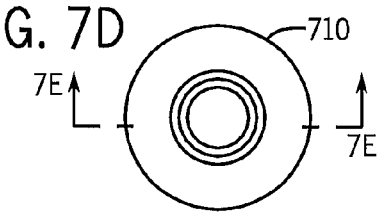
FIG. 7D is a view similar to FIG. 7A, but showing the device indicating a complete use-up condition.
Figure 7E:
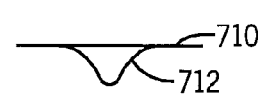
FIG. 7E is a section view taken along line 7E-7E of FIG. 7D.

The device 410 of FIGS. 4A-4E appears almost thermometer like with the remaining liquid clumping towards the bulb area 412A. As shown in FIGS. 4F and 4G varied steps and other configurations can affect the pattern of display moving towards bulb areas 412B and C.

The device 510 of FIGS. 5A-5E appears almost spiral/clock face like with the remaining liquid clumping towards the shallow end of the spiral floor 512.

The device 610 of FIGS. 6A-6E appears like a dot that is disappearing from one side, again with the remaining liquid clumping towards the shallow side along the sloping bottom 612.

The device 710 of FIGS. 7A-7E again appears like a dot that is disappearing from the middle, with the remaining liquid "clumping" radially outwards.

Figure 8:
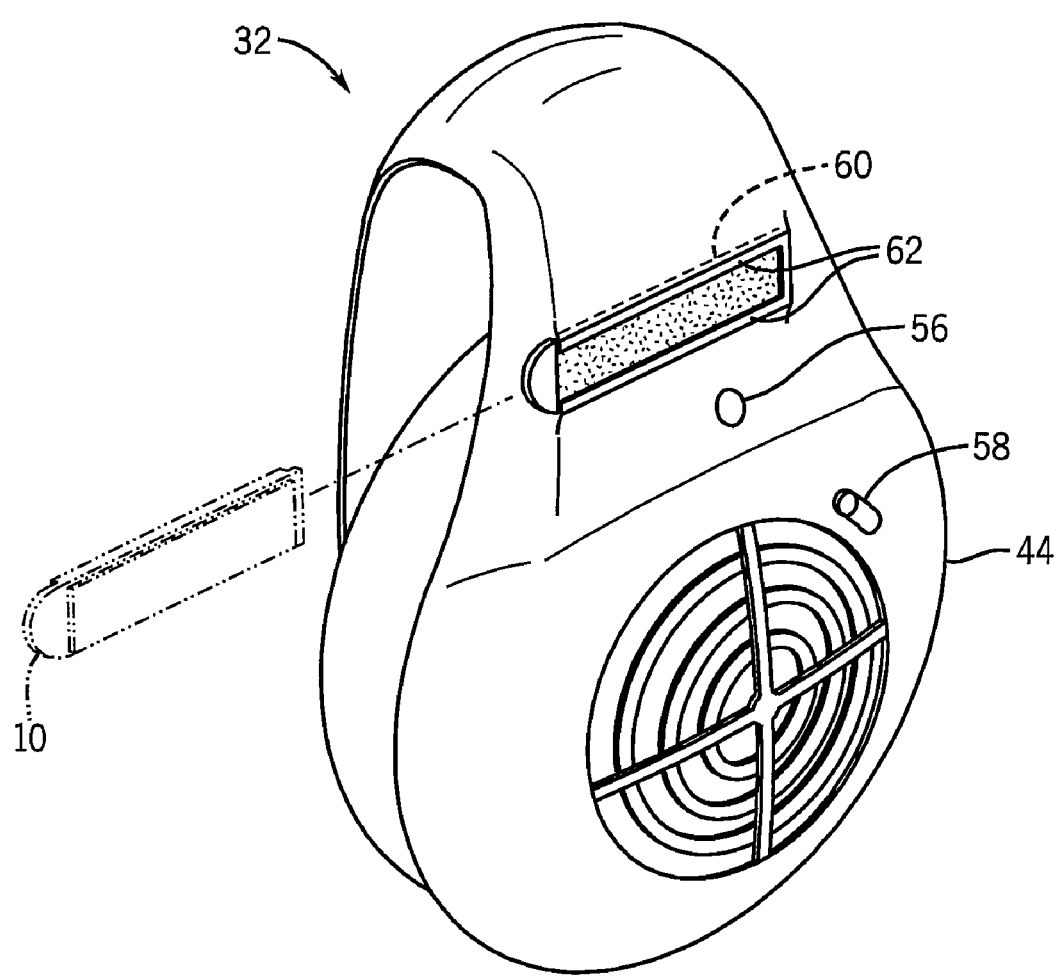
FIG. 8 is a left upper frontal perspective view showing how an indicator of the present invention can be mounted to a portable insect repellent dispenser.
Figure 9:
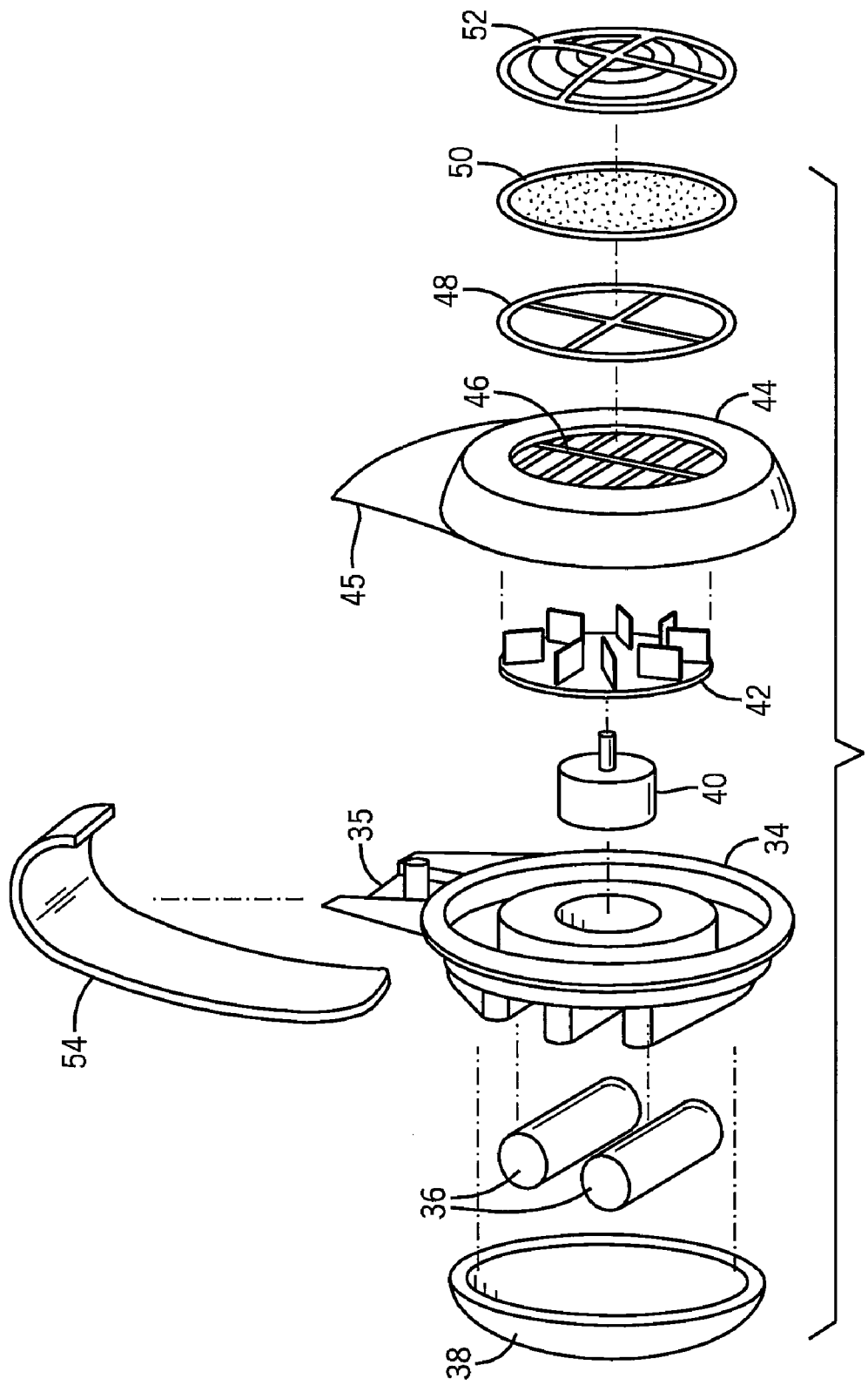
FIG. 9 is an exploded view of the dispenser of FIG. 8.

Indicators of the present invention may be associated with a variety of products, including, but not limited to, air deodorizers, air fragrancers, insect control agent dispensers, and foodstuff packaging. As an example, there is depicted in FIG. 8 an insect repellent dispenser capable of being clipped onto a belt or other clothing item to provide protection without requiring repellent to be placed on the skin or clothing. The FIGS. 8 and 9 device 32 has a front housing 44 and a rear housing 38 configured to retain batteries 36 that power a motor 40 that drives a fan 42. Internal director 34 positions these parts as well as directs air laden with active out a shoot 35.

The front housing 44 has another air channel 45 and has a central inlet 46. An impregnated substrate (e.g. impregnated with transfluthrin) is positioned on a holder 48 under protector grid 52.

A J-shaped clip 54 is attached to the front housing 44. The clip 54 can be used to affix the air-treatment device 32 to a person's belt or other clothing. The front housing 44 may include an indicator light 56 and an on/off switch 58.

When the switch 58 is turned to the on position, the motor 40 is activated, driving the fan 42 to suck air past the substrate 50 into inlet 46, and then out shoot 35. Air treatment chemical volatizes from the substrate 50 into the air flow, and then is directed along the human or their clothing.

Returning to FIG. 8, the front housing 44 of the air-treatment device 32 can, in accordance with the present invention, be provided with a slot (not shown in FIG. 9) for mounting the use-up cue 10. The channel 60 has arms 62 configured to slidably retain the use-up cue 10. Additionally, the use-up cue 10 has a rectangular ear 64 (shown in FIGS. 1-2) that engages a protrusion (not shown) in the channel 60 near the closed end, further securing the use-up cue 10 in the channel 60.

When the personal air-treatment device 32 is first turned on, one can simultaneously remove the peel-off cover 16 from the use-up cue 10. The indicator material 18 will be exposed to a flow of air rushing towards the inlet 46. As the chemical impregnating substrate 50 volatizes, so will the indicator material 18. By proper selection and design, the linear shrinkage of the visible line formed by indicator material 18 can essentially be coordinated with the volatization from the chemical impregnated substrate.

The use-up cue 10 is removable from the air-treatment device 32, thus allowing the use-up cue 10 and the substrate 50 to both be replaced, while preserving the rest of the device 32. Alternatively, the use-up cue 10 may be integrated with the substrate 50 (e.g. along a single slab with a window in the housing providing the ability to view the indicator section).

With respect to the FIG. 8 device, when the volatile air treatment chemical of the substrate 50 is an insecticide and/or insect repellent, organic phosphorous insecticides, lipidamide insecticides, natural repellents as citronella oil, natural pyrethrins and pyrethrum extract, and synthetic pyrethroids are preferred, particularly transfluthrin. Possible solvents for carrying such an air treatment chemical include, but are not limited to, ISOPAR™ C, ISOPAR™ E, ISOPAR™ L, heptane, methanol, acetone, ethanol, isopropyl alcohol, dodecene, and tetraydrofuran. ISOPAR™ C, ISOPAR™ E, and ISOPAR™ L are hydrocarbon solvents of varying chain length and are available from ExxonMobil Chemical Company, and are particularly preferred.

Typically, volatile insect control agents will be applied to a substrate in an organic solvent such as a hydrocarbon. One desirable impregnation formulation for mosquito control is 50% wt. transfluthrin dissolved in ExxonMobil's ISOPAR C hydrocarbon. Alternatively, transfluthrin can be applied to a suitable substrate without use of a solvent.

A wide variety of volatile fragrances may alternatively be used which may optionally also have insect control attributes. Alternatively, some fragrances may be selected that provide a deodorizing function (e.g. certain terpenes). For example, various natural and artificial perfumes may be used. Non-limiting examples of these perfumes include animal-based and plant-based natural perfumes, and artificial perfumes such as alcohols, phenols, aldehydes, ketones, terpenes, and esters.

When a volatile air treatment chemical is a disinfectant, preferred disinfectants include, but are not limited to, glycols, trimethylene, and dipropylene. Organic acids compatible with the use of the substrate 50 and environment may also be used.

The substrate 50 can be fabricated from any material that is capable of absorbing the volatile air treatment chemical, remaining essentially stable under those conditions, and releasing the air treatment chemical either passively, with the aid of air movement, or under heating conditions, whichever is in use. Examples of a suitable substrate 50 include but are not limited to porous sand with a binder such as novolac resin, urethane resins, and highly cross-linked thermoplastics such as cross-linked polyethylene. Alternative substrates include cellulose, glass fiber filters, synthetic paper materials, ceramic materials, textiles, felt-type materials, wovens and nonwovens, bonded or sintered synthetics, natural polymer powders, and the like.

While preferred embodiments of the present invention have been described above, it should be appreciated that the invention could be used in a variety of other embodiments. For example, the indicator could be incorporated on a box exterior for a perishable item, with the idea being that the peel-off cover would be removed at the same time the package is opened by the consumer.

Thus, the principles of the present invention can be applied in a variety of other ways apart from those specifically noted herein and/or depicted in the drawings. Still other modifications may be made without departing from the spirit and scope of the invention. The claims (rather than just the preferred embodiments) should therefore also be reviewed in order to understand the full scope of the invention.

INDUSTRIAL APPLICABILITY

Disclosed herein are indicator devices that display an indication of the portion of useful life remaining for an associated product.

We claim:

1. A useful life indicator, comprising:
   a well having an internal cavity;
   a flowable volatile indicator material positioned within the cavity; and
   a cover member overlying the well;
   wherein the well is configured to cause a remaining portion of the volatile indicator material to clump together in a space below the cover member once another portion of the volatile indicator material in the cavity has volatized from the well, such that a portion of the cavity that prior to said volatization observably contained volatile indicator material appears essentially volatile indicator material free;
   wherein capillary attraction facilitates remaining volatile indicator material clumping together in said space as a portion of the volatile indicator material volatizes out of the well; and
   wherein the well has a shallow portion and a deeper portion, and during use volatile indicator material volatizes in a manner that exposes a floor of the deeper portion before exposing a floor of the shallow portion.

2. The useful life indicator of claim 1, wherein the cover member is in the form of a semi-permeable membrane, and the volatile indicator material is capable of passing through the semi-permeable membrane.

3. The useful life indicator of claim 2, wherein the semi-permeable membrane has an outer peel-off cover removably positioned over the semi-permeable membrane.

4. The useful life indicator of claim 1, wherein the useful life indicator has a display in a form of a rectangle.

5. The useful life indicator of claim 1, wherein the useful life indicator has a display in a form of a gauge.

6. The useful life indicator of claim 1, wherein the useful life indicator has a display that appears thermometer shaped.

7. The useful life indicator of claim 1, wherein the useful life indicator-has a display that appears spiral or clock-shaped.

8. The useful life indicator of claim 1, wherein the useful life indicator has a spot-shaped display which diminishes in size during use from a side of the spot or from a center of the spot.

9. An air treatment control device, comprising:
   holding means for holding and/or dispensing an air treatment chemical from an impregnated substrate;
   a fan; and
   a use-up cue having:
      a well with an internal cavity,
      a flowable volatile indicator material other than the air treatment chemical positioned within the cavity; and
      a cover member overlying the well;
   wherein the well is configured to cause a remaining portion of the volatile indicator material to clump together in a space below the cover member once another portion of the volatile indicator material in the cavity has volatized from the well, such that a portion of the cavity that prior to said volatization observably contained volatile indicator material appears essentially volatile indicator material free;

wherein capillary attraction of the indicator material to itself facilitates remaining volatile indicator material clumping together in said space as a portion of the volatile indicator material volatizes out of the well; and wherein the well has a shallow portion and a deeper portion, and during use volatile indicator material volatizes in a manner that exposes a floor of the deeper portion before exposing a floor of the shallow portion.

10. The device of claim 9, wherein the use-up cue is coordinated with the holding means such that changes in the use-up cue are indicative of an extent of use-up of the air treatment chemical.

11. The device of claim 9, further comprising a heater configured to heat at least the holding means.

12. The device of claim 11, wherein the heater is configured to heat both the holding means and the well.

* * * * *

UNITED STATES PATENT AND TRADEMARK OFFICE
CERTIFICATE OF CORRECTION

| | | |
|---|---|---|
| PATENT NO. | : 7,892,487 B2 | Page 1 of 1 |
| APPLICATION NO. | : 11/609923 | |
| DATED | : February 22, 2011 | |
| INVENTOR(S) | : Joel E. Adair et al. | |

It is certified that error appears in the above-identified patent and that said Letters Patent is hereby corrected as shown below:

Column 8, Line 49 Claim 7: replace "indicator-has" with --indicator has--

Signed and Sealed this
Twentieth Day of September, 2011

David J. Kappos
*Director of the United States Patent and Trademark Office*